(12) United States Patent
Ronsen et al.

(10) Patent No.: US 6,503,927 B1
(45) Date of Patent: *Jan. 7, 2003

(54) AMORPHOUS PAROXETINE COMPOSITION

(75) Inventors: Bruce Ronsen, River Forest, IL (US); Yogesh D. Sadhale, Palatine, IL (US); Ragab El-Rashidy, Deerfield, IL (US)

(73) Assignee: Pentech Pharmaceuticals, Inc., Rolling Meadows, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/428,812

(22) Filed: Oct. 28, 1999

(51) Int. Cl.$^7$ .............................................. A61K 31/445
(52) U.S. Cl. ........................ 514/321; 514/937; 546/197
(58) Field of Search ................................ 514/321, 937; 546/197

(56) References Cited

U.S. PATENT DOCUMENTS

| | | |
|---|---|---|
| 4,007,196 A | 2/1977 | Christensen et al. ........ 546/197 |
| 4,532,318 A * | 7/1985 | Abubakri et al. ............ 528/483 |
| 4,721,723 A | 1/1988 | Barnes et al. ................ 514/321 |
| 5,151,448 A | 9/1992 | Chrenshaw et al. ......... 514/651 |
| 5,276,042 A | 1/1994 | Crenshaw et al. ........... 514/321 |
| 5,672,612 A | 9/1997 | Ronsen et al. ............... 514/338 |
| 5,874,447 A * | 2/1999 | Benneker et al. ............ 514/321 |
| 5,955,475 A * | 9/1999 | Krape et al. ................. 514/321 |
| 6,168,805 B1 * | 2/2001 | Hein ........................... 424/465 |

OTHER PUBLICATIONS

Bull "Introduction to Physical biochemistry" Davias Pubs. (1964) p. 102–105.*
Thomas H. Lowry and Kathlene Schueller Richardson, *Mechanism and Theory in Organic Chemistry*, 2nd Edition, Harper & Row, Publishers, New Yrok, (1981), pp. 264–265.
F. Albert Cotton and Geoffrrey Wilkinson, *Advanced Inorganic Chemistry*, 5th Edition, John Wiley & Sons, New York, (1988), p. 103.

* cited by examiner

*Primary Examiner*—Ceila Chang
(74) *Attorney, Agent, or Firm*—Olson & Hierl, Ltd.

(57) ABSTRACT

A stable amorphous paroxetine hydrochloride composition suitable as a therapeutic agent is prepared employing an aqueous solvent medium containing an acidulant and polyvinylpyrrolidone and drying the resulting solid dispersion. The preferred compositions include amorphous paroxetine hydrochloride, polyvinylpyrrolidone and citric acid.

21 Claims, 4 Drawing Sheets

AMORPHOUS PAROXETINE COMPOSITION

FIELD OF THE INVENTION

This invention relates to an amorphous paroxetine composition suitable as a therapeutic agent.

BACKGROUND OF THE INVENTION

The selective serotonin reuptake inhibitor (SSRI) antidepressants have recently emerged as effective new treatments for patients with premature ejaculation. In general, antidepressants influence more than one neurotransmitter system and have affinity for multiple receptors. This heterogeneity of action produces mixed effects, including those on the sexual response cycle. Sexual dysfunction associated with antidepressants, including delayed and completely abolished ejaculation, has been a subject of numerous case reports, studies, and review articles [for example, *J. Clin. Psychiatry* 54, 209–212, (1993); *J. Clin. Psychopharmacol.* 3, 76–79, (1983); *J. Clin. Psychiatry Mon.* 10, 4–10, (1992); *Depression* 2, 233–240, (1994/1995)]. Because of the lack of abuse potential, relatively benign side effect profile, and fairly consistent reports of delayed ejaculation, SSRI antidepressants seem to be a safe treatment option for patients with premature ejaculation, especially in cases of failed psychological treatment.

The use of the SSRI antidepressant fluoxetine hydrochloride (Prozac®) in this regard has been described in U.S. Pat. No. 5,151,448 to Crenshaw et al. A similar treatment, at a relatively lower dosage of active ingredient, has been described in U.S. Pat. No. 5,276,042 to Crenshaw et al. for the SSRI antidepressant paroxetine hydrochloride (Paxil®). Other anti-anxiety drugs such as chlordiazepoxide (Librium®) and diazepam (Valium®) are not suitable for the treatment of premature ejaculation.

The preparation of a class of SSRI antidepressants has been disclosed in U.S. Pat. No. 4,007,196 to Christensen et al. In Example 2 of this patent, the preparation of (−)-trans-4R-(4'-fluorophenyl)-3S-[(3'4'-methylenedioxy-phenoxy) methyl]-piperidine (generic name paroxetine) is described (formula A),

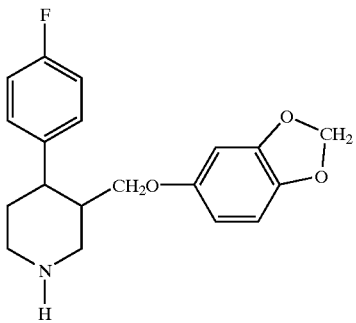

(A)

wherein paroxetine is obtained as a free base then converted to its maleic acid salt. The use of the acetate salt of paroxetine has been described [*Psychopharmacology* 57, 151–153 (1978); *Psychopharmacology* 68, 229–233 (1980); *European Journal of Pharmacology* 47, 351–358 (1978)].

In general the hydrochloride salt of a basic compound, such as paroxetine, is preferred for therapeutic use because of its physiological acceptability. There has been limited use of the hydrochloride salt of paroxetine in aqueous solution [*Acta. Pharmacol. Et Toxicol.* 44, 289–295 (1979)]. U.S. Pat. No. 4,721,723 to Barnes et al. disclosed the preparation of a crystalline paroxetine hydrochloride hemihydrate in organic solvent media. However, this particular process requires considerable post-synthetic treatment of the product in order to remove the organic solvent and recrystallization procedures in order to obtain a useful purified crystalline form, which adds to the difficulty and overall cost of production. Non-crystalline, i.e., amorphous, paroxetine hydrochloride has been reported by Barnes et al. to be an undesirably hygroscopic solid of poor handling qualities for commercial use.

Some success in preparing a free-flowing, substantially non-hygroscopic solid form of amorphous paroxetine hydrochloride-ethanol composition was disclosed in U.S. Pat. No. 5,672,612 to Ronsen et al. The amorphous paroxetine hydrochloride-ethanol composition was amenable to incorporation into both tablet and suppository dosage forms, and suitable as a therapeutic agent, especially for the treatment of premature ejaculation.

However, there is still a need and desire for the preparation of solid dispersions of amorphous paroxetine hydrochloride composition substantially free of organic solvents. It has been surprisingly found that solid dispersion of amorphous paroxetine hydrochloride can be efficiently prepared from an aqueous solvent medium.

SUMMARY OF THE INVENTION

Compositions of amorphous paroxetine hydrochloride having at least one non-ionic water-soluble polymer and an acidulant compound, as well as methods for production of such compositions from an aqueous solvent-based medium are disclosed. A preferred water-soluble polymer is polyvinylpyrrolidone (PVP).

The present inventive method preferably produces substantially stable amorphous paroxetine hydrochloride solid dispersion compositions from an aqueous solution of paroxetine hydrochloride, polyvinylpyrrolidone and an acidulant followed by drying of the product. The term "acidulant" as used herein refers to nontoxic biocompatible organic and inorganic acids having a dissociation constant value (pKa) in the range of about 2 to about 7. Optionally, a water-miscible co-solvent capable of forming an azeotropic mixture with water can be present in the aqueous solution.

Addition of polyvinylpyrrolidone to the composition is useful in improving the stability of the amorphous paroxetine hydrochloride composition by preventing the spontaneous crystallization of the amorphous form to the crystalline form. Preferred acidulants are hydroxycarboxylic acids. A preferred hydroxycarboxylic acid is citric acid.

In a preferred method aspect, the amount of citric acid is in the range of about 1 to about 10 weight percent based on the weight of paroxetine hydrochloride, and preferably is in the amount of about 3 weight percent. The molar ratio of polyvinylpyrrolidone to paroxetine hydrochloride preferably is in the range of about 100 percent to about 300% percent. Drying can be carried out by rotary evaporation, spray drying, oven drying and the like.

A preferred amorphous paroxetine hydrochloride can be prepared according to the procedure set forth in U.S. Pat. No. 5,672,612 to Ronsen et al. and is incorporated herein by reference.

This invention beneficially provides for the efficient preparation of stable, solid dispersions of amorphous paroxetine hydrochloride compositions in an environmentally acceptable process. The inventive process avoids the inherent problems associated with the use of non-aqueous solvents and eliminates the additional steps and costs associated with preparation, of crystalline forms. The amorphous paroxetine composition embodying the present invention is well suited for the preparation of tablet dosage forms containing paroxetine.

DETAILED DESCRIPTION OF THE PREFERRED EMBODIMENTS

Figure 1:
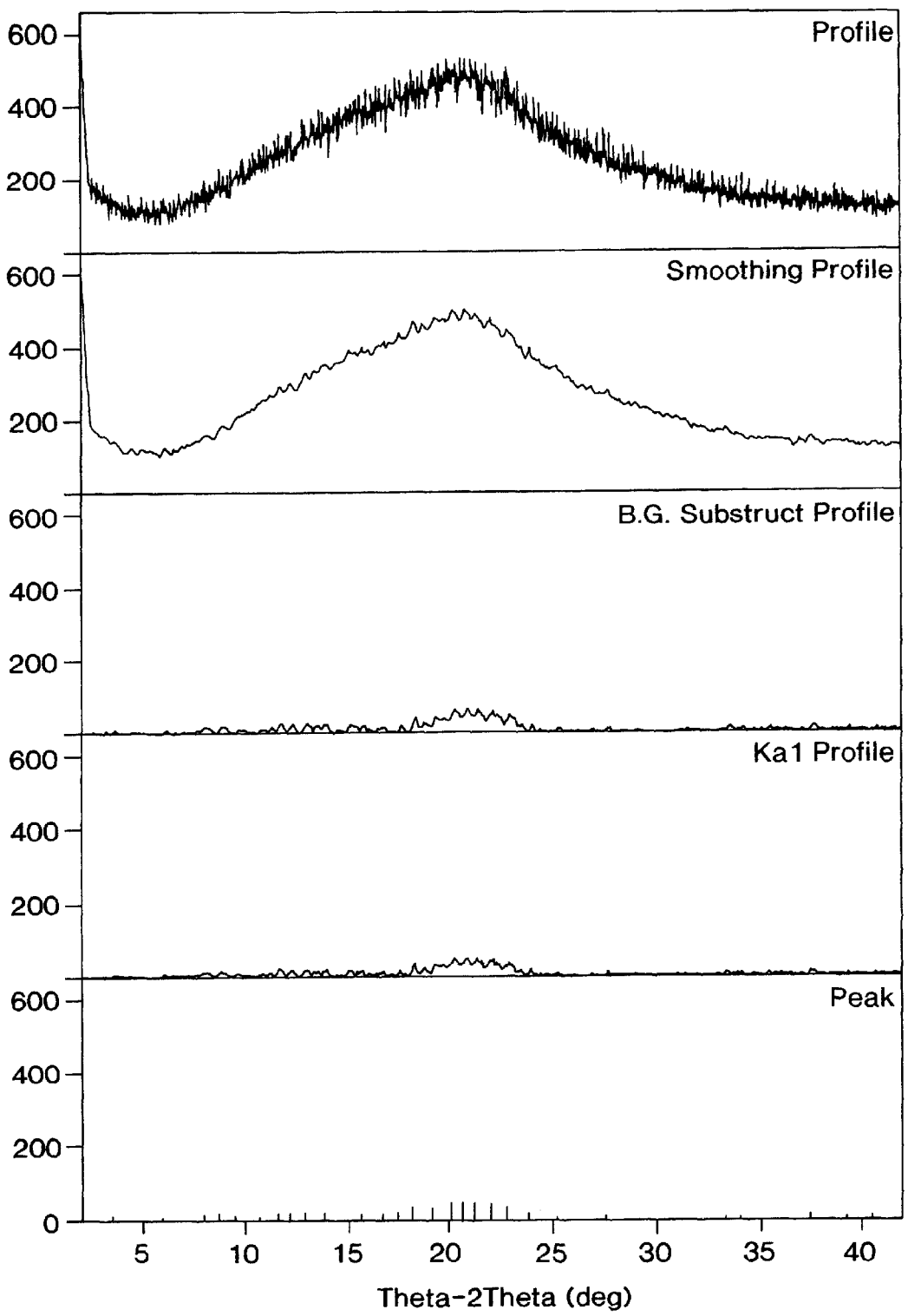
FIG. 1 is a powder XRD spectrum of rotary evaporated, vacuum dried aqueous solvent based amorphous paroxetine hydrochloride solid dispersion.

The term "aqueous solvent based" or "aqueous solvent medium" as used herein means that the solvent is water or optionally a mixture of water and a water-miscible co-solvent capable of forming an azeotrope with water. Water is the preferred solvent. Co-solvents, when present, preferably are absolute ethanol, isopropyl alcohol and the like.

In a preferred method aspect, a solid dispersion of amorphous paroxetine hydrochloride is preferably obtained by combining previously prepared amorphous paroxetine hydrochloride with an aqueous solution of polyvinylpyrrolidone and citric acid, followed by drying. The drying step can be effected by rotary evaporation (rotavapping), spray-drying, vacuum drying, oven drying and the like.

In one method aspect, the amorphous paroxetine hydrochloride can be obtained as a solid form of paroxetine hydrochloride-ethanol according to the procedure set forth in U.S. Pat. No. 5,672,612, incorporated herein by reference. The amorphous paroxetine hydrochloride solid is then added to an aqueous solution of polyvinylpyrrolidone and citric acid. The molar ratio of polyvinylpyrrolidone to paroxetine hydrochloride preferably being in the range of about 100 weight percent to about 300 weight percent of the weight of the paroxetine hydrochloride. The amount of citric acid can be in the range of about 1 weight percent to about 10 weight percent based on the weight of paroxetine hydrochloride, and preferably is in the amount of about 3 weight percent.

The process temperature is preferably in the range of about 15 degrees C. to about 40 degrees C. The process is carried out for a time period sufficient to dissolve the reaction components in the aqueous solvent medium. Preferably the process time is in the range of about 10 minutes to about 40 minutes. The resulting solution is then dried by rotary evaporation, vacuum drying, convention oven drying, spray drying and the like to obtain the desired, substantially solid amorphous paroxetine hydrochloride composition. The amount of water present in the final product relative to paroxetine hydrochloride preferably is not more than about 10 weight percent, more preferably in the range of about 3 to about 6 weight percent.

Polyvinylpyrrolidone ("PVP") is a polyamide that possesses unusual complexing and colloidal properties and is physiologically inert. Several grades are manufactured and sold in the United States under a variety of names: PVP, Plasdone, Polyclar A T, Peregal S T, Kollidone, and Albigen A. See Davidson, *Handbook of Water-Soluble Gums and Resins* (McGraw-Hill Book Company). PVP is commercially available in four viscosity grades identified by their K-value: K-15, K-30, K-60, and K-90. The number average of the molecular weights for these grades are about 10,000, 40,000, 160,000 and 360,000, respectively. The K-value or molecular weight is a significant determinant in the properties of the product. In the present invention the preferred grade of polyvinylpyrrolidone is K-30 ("PVP-30") and is preferably present in the amount from about 100 weight percent to about 300 weight percent based on the weight of the amorphous paroxetine hydrochloride.

The polymer molecular weight will depend upon the requirements of the intended end use of the drug formulation. The polymer molecular weight is one factor to be considered for drug compatibility and an appropriate polymer molecular weight can be readily determined by one of ordinary skill in the art without undue experimentation.

The addition of one or more acidulant compounds to the composition is also useful in improving the stability of the amorphous paroxetine composition as measured by color and by paroxetine content. Suitable acidulants are substantially non-toxic organic acids and inorganic acids or a combination of such acids having a dissociation constant value (pKa) in the range of about 2 to about 7, employed in the pharmaceutical arts.

Suitable organic acids can be aliphatic carboxylic acids such as acetic acid, maleic acid, malonic acid, succinic acid, and the like or preferably hydroxycarboxylic acids, such as citric acid, malic acid, tartaric acid, lactic acid and the like. The preferred hydroxycarboxylic acid is citric acid preferably present in an amount in the range of about one weight percent to about 10 weight percent, more preferably in an amount of about 3 weight percent, based on the weight of paroxetine hydrochloride.

Suitable inorganic acids can include hydrochloric acid, nitric acid, phosphoric acid, sulfuric acid and the like, so long as they do not interfere with the therapeutic efficacy of the amorphous paroxetine hydrochloride.

It may be desired to deliver the amorphous paroxetine hydrochloride in a dosage form which provides for controlled or sustained release of the active agent. In such a case, the delivery system of the dosage form preferably comprises a polymeric matrix. Preferably, the polymeric matrix comprises a pharmaceutically acceptable, biocompatible, biodegradable hydrophilic polymer. The hydrophilic polymers may be natural, modified natural or synthetic polymers. A number of pharmaceutically acceptable hydrophilic polymers are known in the art suitable for use as the polymeric matrix of the delivery system of the invention.

For example, the hydrophilic polymer can be as gelatin, ovalbumin, soybean proteins, gum arabic, starch, modified starch, methylcellulose, hydroxypropyl cellulose, hydroxypropylmethyl cellulose and the like polymers and mixtures thereof.

The amorphous paroxetine hydrochloride composition of the present invention can also include pharmaceutically acceptable excipients, such as carriers, diluents, binders, disintegrants, coloring agents, flavoring agents, lubricants, preservatives and the like to facilitate the formation of dosage forms such as tablets or capsules.

Excipients known to one skilled in the art can include polyglycols, such as polyethylene glycol ("PEG"), propylene glycol ("PG"), glycerin and the like with polyethylene glycol and derivatives thereof particularly preferred. Suitable polyethylene glycol derivatives include polyethylene glycol fatty acid esters, for example, polyethylene glycol monostearate, polyethylene glycol sorbitan esters, e.g., polysorbates, and the like.

Other conventional nontoxic, pharmaceutically acceptable excipients can include, for example, pharmaceutical grades of sugars, such as mannitol, lactose, glucose, and sucrose, starch, magnesium stearate, sodium saccharin, talc, cellulose, magnesium carbonate, and the like.

The amount of paroxetine hydrochloride administered, and the dosing regimen used will depend on the age and general condition of the subject being treated, the severity of the subject's condition, and the judgment of the prescribing physician.

The following examples are merely illustrative and are not intended to limit the scope and spirit of the invention except as defined by the appended claims.

EXAMPLE 1

Preparation of Amorphous Paroxetine HCl Composition: Vacuum Drying Method

About 0.24 grams of citric acid was dissolved in about 1000 ml of deionized water, followed by the addition of about 4 grams of PVP-30, in a beaker. After the two components were completely dissolved, about 3.76 grams of previously prepared amorphous paroxetine hydrochloride was added to the aqueous solution with constant stirring. The aqueous solution was slightly warmed to just under 40° C. to aid dissolution. Once all the paroxetine hydrochloride was in solution, the solution was transferred to a 2-Liter (L) volume round-bottomed flask and the flask was mounted on a rotary evaporator and set in a heated water bath. The water was evaporated from the solution at a water-bath temperature of about 80° C. and rotation speed of about 200 rpm. When the contents of the flask were visually judged to be essentially dry, the contents of the flask were allowed to dry under vacuum at a water-bath temperature of about 80° C. for approximately an additional 1 hour. This resulted in a slightly yellowish, glassy solid. After about 1 hour the flask was removed from the water bath, and the contents allowed to cool to a solid dispersion which was then recovered by scraping. The recovered solid dispersion product was weighed and the yield was determined to be about 7.8 grams (97.5%).

The composition of the solid product was tested by Fourier Transform Infra Red (FTIR) technique. A Nicolet Magna IR System 750 Fourier Transform Infrared Spectrometer controlled via Nicolet Omnic ESP® software was used to obtain the spectra. A KBr beamsplitter was used and data was collected over 4000–400 $cm^{-1}$ with a resolution of 4 $cm^{-1}$. An MCT-A detector, cooled with liquid nitrogen, was used. The sample compartment was under constant nitrogen purge. The aperture was set at 28, the micro velocity was 1.8988 and the gain setting was 1. The contact; sampler attachment, which is a horizontal internal reflection accessory, with a trough cell, containing the ZnSe 45° ATR crystal, was used. The background spectrum was air. The spectrum was obtained by averaging 100 scans. The findings were consistent with published spectra for paroxetine.

Residual moisture was determined by Karl-Fisher coulometric method using a Mettler DL37 Karl Fisher Titrator. The samples were dissolved in methanol and triplicate measurements were taken. The moisture content for the sample was determined to be about 5.3%.

Differential Scanning Calorimetry (DSC) was performed on the samples using a Perkin-Elmer DSC7 system equipped with a TAC 7/DX Thermal Analysis Controller. Cooling was provided by a Perkin-Elmer Intracooler, which was turned on one hour prior to the initiation of the calibration run. Perkin-Elmer Thermal Analysis software version 4.0 was used to collect and analyze data, using a Digital 466 D2LP computer under the UNIX operating system. Scans were obtained at 10° C./minute under a constant nitrogen purge. The DSC pans were aluminum, Perkin-Elmer No. 0219-0062 volatile sample pans, and were crimped using the Perkin-Elmer sample sealing device. Sample weights were obtained using the Mettler UMT2 microbalance. The melting peak due to the crystalline paroxetine hydrochloride was not found in the samples scanned.

X-ray powder crystallography was conducted on the sample and produced the diffraction pattern shown in FIG. 1. Powder diffractograms were recorded on an automated Shimadzu XRD-6000 X-ray diffractometer using Shimadzu XRD-6000 v 2.5 diffraction software. Recording conditions were 30 kV, 30 mA, scan rate 2.0000°/min, scan range 2–42°, divergence slit 1.0000°, scanner slit 1.000° and receiving slit 0.15 mm. The halo effect is clearly seen and the intensity is small. This spectrum is consistent with an amorphous solid form.

About one-half of the recovered amount of vacuum dried solid dispersion was isolated and the following humidity, isotherm study was also performed. Approximately 0.38 grams of the solid dispersion were separately weighed into each of 8 glass vials and the weight of each capped vial along with its contents was recorded. All the vials except the $T_0$ sample were placed, with their caps removed, in the stability chamber at an ambient temperature of about 30° C. and ambient relative humidity of about 60%. After periods of 6 hours, 12 hours, 1 day, 4 days, 7 days, 2 weeks and 4 weeks, one vial each for the dried solid dispersions was removed and immediately capped. The vial was weighed again and the weight recorded. After weighing the vial, a small sample (about 1 to 2 mg) from the vial was observed under polarized-light microscope for birefringence using a Leica DMLB optical microscope. The remaining portion of the rotary evaporated, vacuum dried sample was analyzed by DSC, FTIR, X-Ray Diffraction (XRD) and for % moisture.

TABLE 1 summarizes the results of all tests for the rotary evaporated, vacuum dried aqueous solid dispersions of amorphous phenoxetine hydrochloride.

TABLE 1

Summary of results for the rotary evaporated, vacuum dried, aqueous solid dispersion

| Sampling Time | Weight Change | Moisture (%) | No birefringence Optical Microscopy | No endotherms from 130–150° C. DSC | No bands from 3350–3500 $cm^{-1}$ FTIR | Amorphous 'halo' pattern X-Ray Diffraction |
|---|---|---|---|---|---|---|
| $T_0$ | — | 5.3 | Conforms | Conforms | Conforms | Conforms |
| 6 hours | 0.00 | 5.9 | Conforms | Conforms | Conforms | Conforms |
| 12 hours | 2.7 | 5.1 | Conforms | Conforms | Conforms | Conforms |

TABLE 1-continued

Summary of results for the rotary evaporated, vacuum dried, aqueous solid dispersion

| Sampling Time | Weight Change | Moisture (%) | No birefringence Optical Microscopy | No endotherms from 130–150° C. DSC | No bands from 3350–3500 cm$^{-1}$ FTIR | Amorphous 'halo' pattern X-Ray Diffraction |
|---|---|---|---|---|---|---|
| 1 day | 2.6 | 5.2 | Conforms | Conforms | Conforms | Conforms |
| 4 days | 2.7 | 4.9 | Conforms | Conforms | Insufficient Sample | Conforms |
| 7 days | 5.4 | 5.3 | Slight birefringence in some particles | Conforms | Conforms | Conforms |
| 2 weeks | 2.6 | 6.6 | Slight birefringence in some particles | Conforms | Conforms | Conforms |
| 4 weeks | 5.4 | 7.2 | Conforms | Conforms | Conforms | Insufficient Sample |

EXAMPLE 2

Preparation of Amorphous Paroxetine HCl Composition: Vacuum Drying Method Followed By Convection Oven Drying The remaining half-portion of the rotary evaporated, vacuum dried amorphous paroxetine hydrochloride prepared by the procedure of Example 1 was lightly ground and further dried in a regular convection oven at a temperature of about 60° C. for about 22.5 hours.

Figure 2:
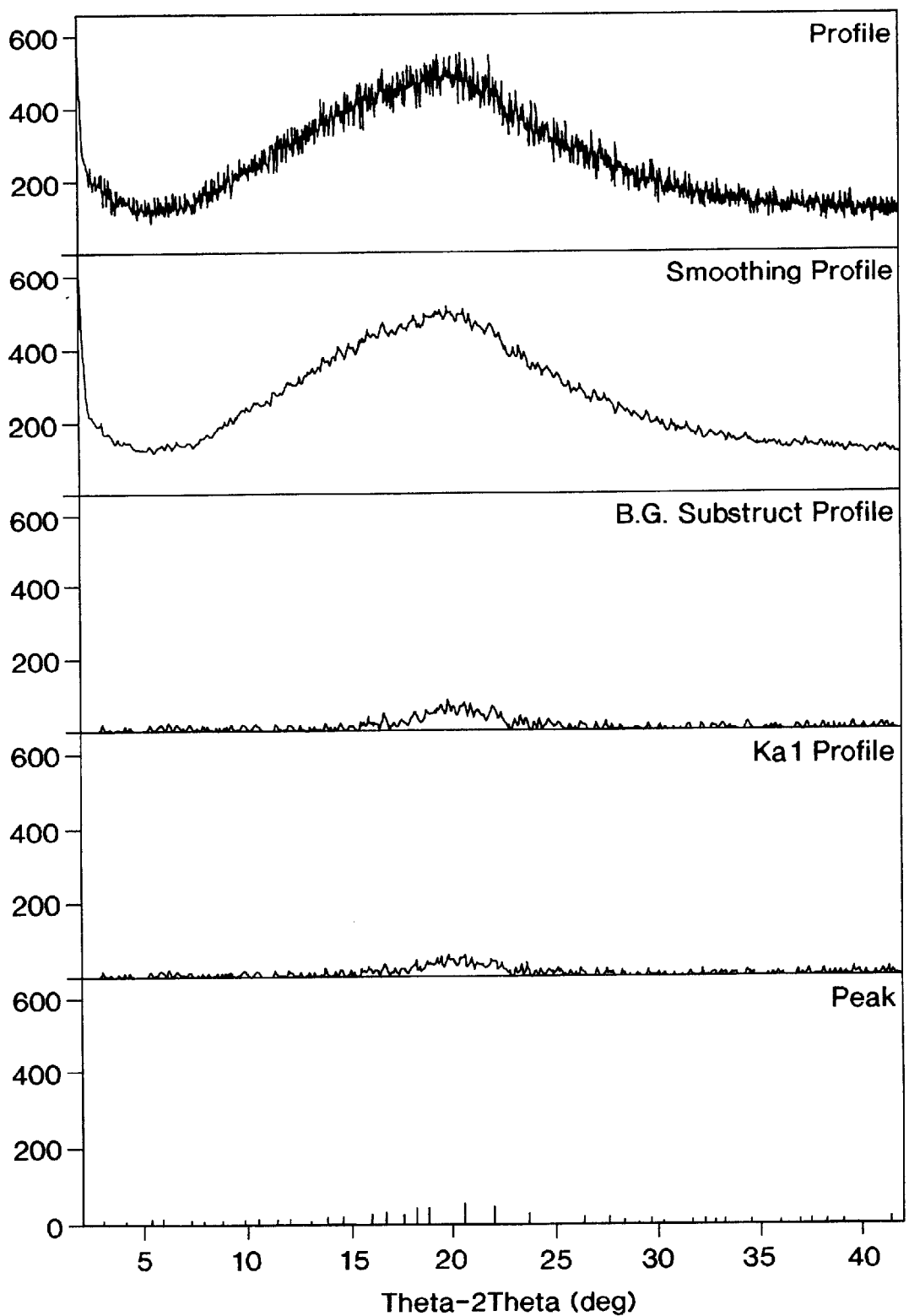
FIG. 2 is a powder XRD spectrum of rotary evaporated, vacuum dried and convection oven dried aqueous solvent based amorphous paroxetine hydrochloride solid dispersion.

Residual moisture was determined by Karl-Fisher coulometric method using a Mettler DL37 Karl Fisher Titrator. The samples were dissolved in methanol and triplicate measurements were taken. The moisture content for the sample at the end of about 22.5 hours of drying at about 60° C. in a convection oven was determined to be about 3.1%. X-ray powder crystallography was conducted on the sample and produced the diffraction pattern shown in FIG. 2. This spectrum is consistent with an amorphous form, and was confirmed by DSC and FTIR analysis.

A humidity isotherm study was performed on the convection oven dried solid dispersion. Approximately 0.38 grams of the dried solid dispersion were separately weighed into each of 8 glass vials and the weight of each capped vial along with its contents was recorded. All the vials except the T$_0$ sample were placed, with their caps removed, in the stability chamber at an ambient temperature of about 30° C. and ambient relative humidity of about 60%. After periods of 6 hours, 12 hours, 1 day, 7 days, 2 weeks and 4 weeks, one vial each for the dried solid dispersions was removed and immediately capped. The vial was weighed again and the weight recorded. After weighing the vial, a small sample (about 1 to 2 mg) from the vial was observed under polarized-light microscope for birefringence using a Leica DMLB; optical microscope. The remaining amount of the convection oven dried sample was analyzed by DSC, FTIR, XRD and for % moisture.

TABLE 2 summarizes the results of all tests for the rotary evaporated, vacuum dried and convection oven dried aqueous solid dispersions.

TABLE 2

Summary of results for the rotary evaporated, vacuum dried and convection oven dried aqueous solid dispersion

| Sampling Time | Weight Change | Moisture (%) | No birefringence Optical Microscopy | No endotherms from 130–150° C. DSC | No bands from 3350–3500 cm$^{-1}$ FTIR | Amorphous 'halo' pattern X-Ray Diffraction |
|---|---|---|---|---|---|---|
| T$_0$ | — | 3.1 | Conforms | Conforms | Conforms | Conforms |
| 6 hours | 5.3 | 4.3 | Conforms | Conforms | Conforms | Conforms |
| 12 hours | 7.9 | 4.9 | Conforms | Conforms | Conforms | Conforms |
| 1 day | 8.3 | 5.2 | Conforms | Conforms | Conforms | Conforms |
| 7 days | 10.5 | 7 | Slight birefringence in some particles | Conforms | Conforms | Conforms |
| 2 weeks | 10.0 | 8.3 | Slight birefringence in some particles | Conforms | Conforms | Conforms |
| 4 weeks | 13.2 | 8 | Slight birefringence in some particles | Conforms | Conforms | Conforms |

EXAMPLE 3

Preparation of Amorphous Paroxetine HCl Composition: Spray Drying Method

About 0.18 grams of citric acid were dissolved in about 1000 ml of deionized water by stirring. When the citric acid had completely dissolved, about 2.82 grams of previously prepared amorphous paroxetine hydrochloride were slowly added to the solution with stirring. The aqueous solution was heated to no more than about 40° C., if required, to aid dissolution. After all the paroxetine hydrochloride had dissolved, about 3 grams of PVP-30 was slowly added to the solution with stirring and dissolved. The aqueous solution was filtered while hot, through a Millipore white, gridded (type HA) filter of 0.45μ pore size to ensure the complete removal of any small seed crystals that may be present in the solution. One half of the solution was then spray-dried in a cyclone spray drier.

| | |
|---|---|
| Heating Control: | 14.5 |
| Inlet Temperature: | 199° C. |
| Outlet Temperature: | 125° C. |
| Aspirator Control: | 14.5 |
| Aspiration Pressure: | −42 mbar |
| Pump Control: | 15 |
| Flow Indicator Reading: | 300 |

Spray-drying the solution using a Büchi 190 Mini Spray Dryer with the above parameters resulted in the collection of a dry yellowish powder along the inner walls of the cyclone. Some of the product also collected in the product collector below the cyclone but the amount was negligible compared to that inside the cyclone. A small amount of the product was also found in the plug of cotton used to block the aspirator from sucking up the product. The amount recovered by scraping the cyclone and the product collector was about 1.5 grams with about 1 gram lost to the cotton plug. This resulted in a yield of about 60%.

The composition of the solid was tested by FTIR. A Nicolet Magna IR System 750 Fourier Transform Infrared Spectrometer controlled via Nicolet Omnic ESP® software was used to obtain the spectra. A KBr beamsplitter was used and data was collected over 4000–400 cm$^{-1}$ with a resolution of 4 cm$^{-1}$. An MCT-A detector, cooled with liquid nitrogen, was used. The sample compartment was under constant nitrogen purge. The aperture was set at 28, the micro velocity was 1.8988 and the gain setting was 1. The contact sampler attachment, which is a horizontal internal reflection accessory, with a trough cell, containing the ZnSe 45° ATR crystal, was used. The background spectrum was air. The spectrum was obtained by averaging 100 scans. The findings were consistent with published spectra for paroxetine.

Differential scanning calorimetry was performed on the samples using a Perkin-Elmer DSC7 system equipped with a TAC 7/DX Thermal Analysis Controller. Cooling was provided by a Perkin-Elmer Intracooler, which was turned on one hour prior to the initiation of the calibration run. Perkin-Elmer Thermal Analysis software version 4.0 was used to collect and analyze data, using a Digital 466 D2LP computer under the UNIX operating system. Scans were obtained at 10° C./minute under a constant nitrogen purge. The DSC pans were aluminum, Perkin-Elmer No. 0219-0062 volatile sample pans, and were crimped using the Perkin-Elmer sample sealing device. Sample weights were obtained using the Mettler UMT2 microbalance. The melting peak due to the crystalline paroxetine hydrochloride was not found in the samples scanned.

Figure 3:
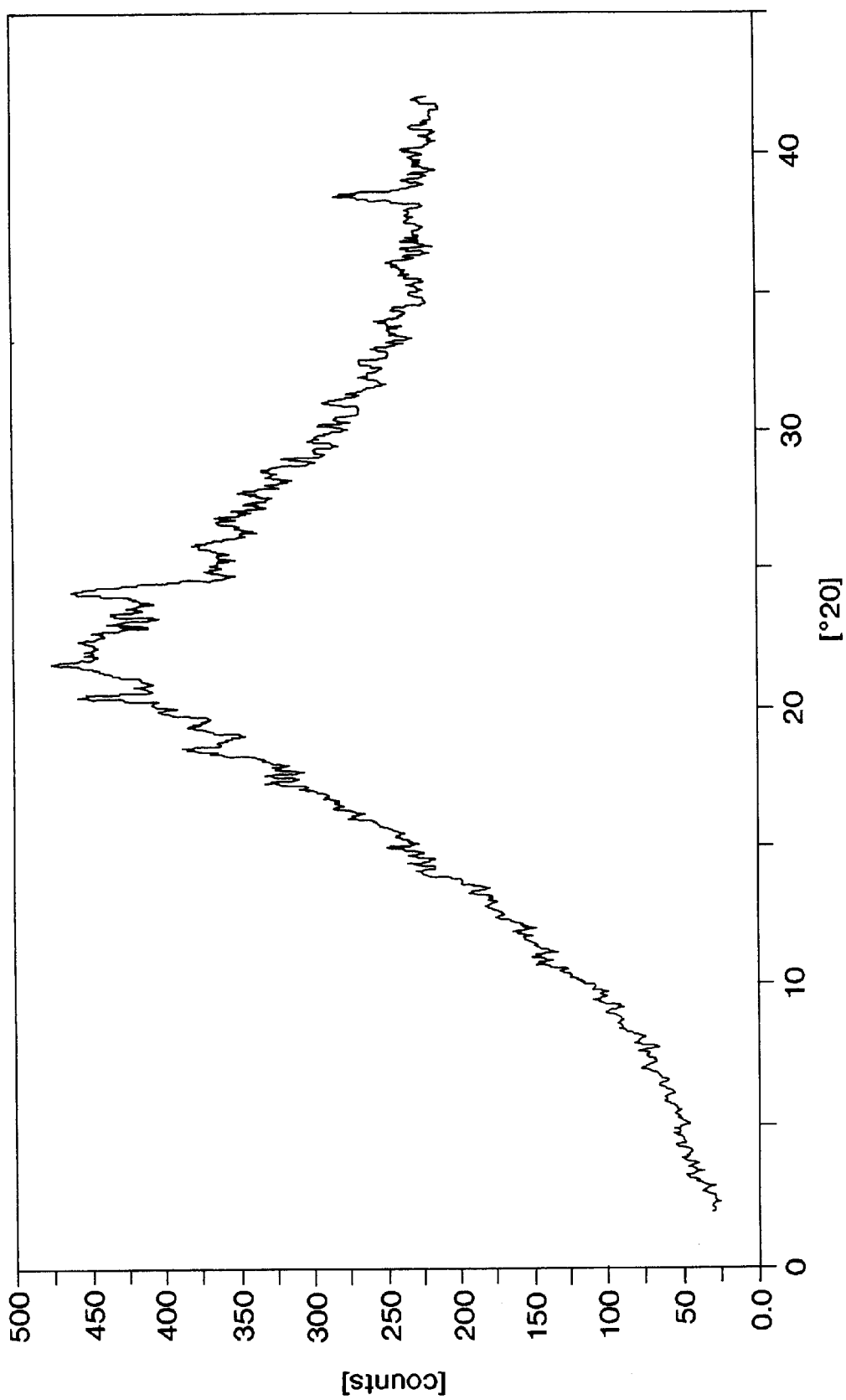
FIG. 3 is a powder XRD spectrum of spray-dried aqueous solvent based amorphous paroxetine hydrochloride solid dispersion.

X-ray powder crystallography was conducted on the sample and produced the diffraction pattern shown in FIG. 3. Powder diffractograms were recorded on an automated Shimadzu XRD-6000 X-ray diffractometer using Shimadzu XRD-6000 v 2.5 diffraction software. Recording conditions were 30 kV, 30 mA, scan rate 2.0000°/min, scan range 2–42°, divergence slit 1.0000°, scanner slit 1.000° and receiving slit 0.15 mm. The halo effect is clearly seen and the intensity is small. This spectrum was consistent with an amorphous solid form.

When the sample was observed under polarized-light microscope for birefringence using a using a Leice DMLB optical microscope, no birefringence was observed indicating that the sample was amorphous.

EXAMPLE 4

Preparation of Amorphous Paroxetine HCl Compositions: Rotary Evaporation Method

Figure 4:
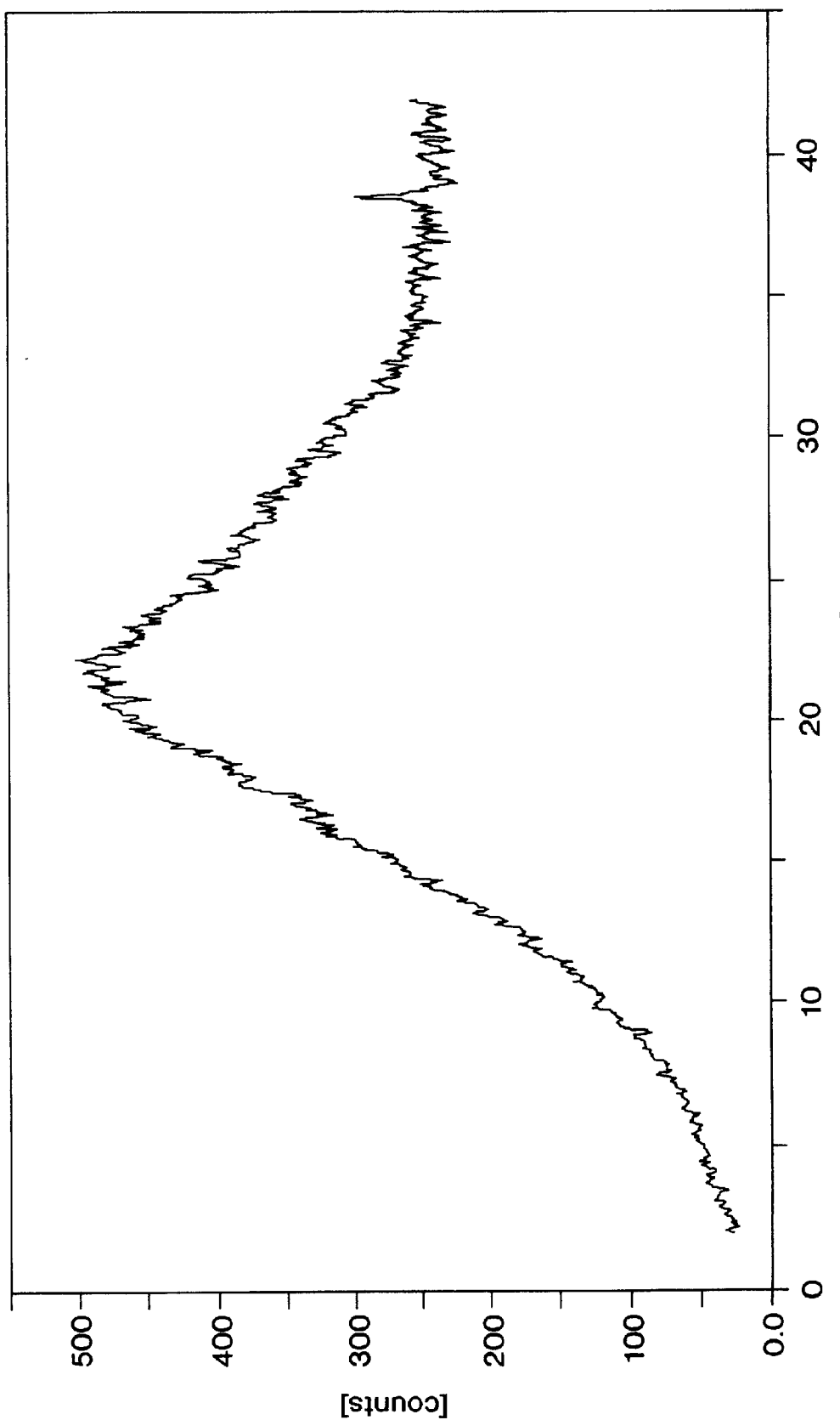
FIG. 4 is a powder XRD spectrum of rotary evaporated aqueous solvent based amorphous paroxetine hydrochloride.

The remaining half-portion of the paroxetine hydrochloride solution prepared by the procedure of Example 3 was rotary evaporated in a flask mounted on a rotary evaporator and set in a heated water bath. The water was evaporated from the solution at a water-bath temperature of about 80° C. and rotation speed of about 200 rpm. When the contents of the flask were visually judged to be essentially dry, the contents were allowed to cool to a solid dispersion which was then recovered by scraping. This resulted in a slightly yellowish, glassy solid. The recovered solid dispersion product was weighed and the yield was determined to be about 2 g or about 80%. X-ray powder crystallography was conducted on the sample and produced the diffraction pattern shown in FIG. 4. The typical halo effect pattern of the spectra is consistent with the amorphous solid form. The amorphous nature of the solid dispersion was also confirmed by DSC, FTIR and Optical Microscopy analysis as described in Example 3.

The foregoing examples showed that solid dispersions of amorphous paroxetine hydrochloride produced from aqueous solvent based medium remained amorphous even after prolonged exposure to ambient relative humidity of 30% to 60%. The absence of birefringence indicates the amorphous nature of the solid dispersions. Although some of the samples showed what appears to be birefringence, the DSC, FTIR and XRD analysis provided categorical evidence that none of the solid dispersions were crystalline supporting the presence of the amorphous form. The results showed that the amorphous nature of the paroxetine hydrochloride was not affected by the drying step.

We claim:

1. A stable, solid dispersion of an amorphous paroxetine composition comprising:
   an amorphous paroxetine hydrochloride salt;
   polyvinylpyrrolidone in an amount of about 100 percent to about 300 percent by weight, based on the weight of the amorphous paroxetine hydrochloride salt; and
   a nontoxic acidulant which is an organic acid having a dissociation constant value (pKa) in the range of about 2 to about 7 and in the amount of about 1 percent to about 10 percent by weight, based on the amorphous paroxetine hydrochloride salt.

2. The amorphous paroxetine composition of claim 1, wherein the nontoxic acidulant is a hydroxycarboxylic acid.

3. The amorphous paroxetine composition of claim 1, wherein the nontoxic acidulant is citric acid.

4. The amorphous paroxetine composition of claim 1, wherein the polyvinylpyrrolidone has a viscosity grade of K-30.

5. The amorphous paroxetine composition of claim 1 further comprising a polymeric matrix.

6. The amorphous paroxetine composition of claim 5 wherein the polymeric matrix comprises a hydrophilic polymer.

7. The amorphous paroxetine composition of claim 1 further comprising one or more pharmaceutically acceptable excipients.

8. The composition of claim 1 in tablet form.

9. A method of making a stable amorphous paroxetine hydrochloride composition comprising the steps of:
   1) combining previously prepared amorphous paroxetine hydrochloride and an aqueous solution containing an acidulant;
   2) dissolving the amorphous paroxetine hydrochloride in the resulting aqueous solvent medium by heating to a temperature in the range of about 15 degrees C. to about 40 degrees C.;
   3) adding polyvinylpyrrolidone to the resulting aqueous solution and dispersing therein; and thereafter
   4) drying the resulting solid dispersion.

10. The method of claim 9 wherein steps 1 and 3 are performed simultaneously.

11. The method of claim 9 wherein the molar ratio of polyvinylpyrrolidone to paroxetine hydrochloride is in the range of about 100 to about 300 percent by weight based on the paroxetine hydrochloride.

12. The method of claim 9 wherein the weight ratio of the acidulant to paroxetine hydrochloride is in the range of about 1 percent to about 10 percent by weight, based on the paroxetine hydrochloride.

13. The method of claim 9 wherein the acidulant is an organic acid.

14. The method of claim 9 wherein the acidulant is a hydroxycarboxylic acid.

15. The method of claim 9 wherein the acidulant is citric acid.

16. The method of claim 9 wherein the aqueous solution further includes a water-miscible solvent.

17. The method of claim 16 wherein the water-miscible solvent forms an azeotrope with water.

18. The method of claim 17 wherein the water-miscible solvent is selected from the group consisting of ethanol and isopropyl alcohol.

19. The method of claim 9 wherein the drying step is effected by spray drying.

20. The method of claim 9 wherein the drying step is effected in a rotary evaporator.

21. The method of claim 9 further including the step of recovering the amorphous paroxetine hydrochloride solid composition.

* * * * *